(12) United States Patent
Numata (10) Patent No.: US 12,267,603 B2
(45) Date of Patent: Apr. 1, 2025

(54) PHOTOELECTRIC CONVERSION DEVICE, IMAGING DEVICE, CONTROL METHOD, AND STORAGE MEDIUM

(71) Applicant: CANON KABUSHIKI KAISHA, Tokyo (JP)

(72) Inventor: Aihiko Numata, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 269 days.

(21) Appl. No.: 17/933,765

(22) Filed: Sep. 20, 2022

(65) Prior Publication Data
US 2023/0095243 A1   Mar. 30, 2023

(30) Foreign Application Priority Data
Sep. 24, 2021   (JP) ................. 2021-155380

(51) Int. Cl.
H04N 25/10 (2023.01)
G16H 30/00 (2018.01)
H04N 23/95 (2023.01)

(52) U.S. Cl.
CPC ............ *H04N 25/10* (2023.01); *G16H 30/00* (2018.01); *H04N 23/95* (2023.01)

(58) Field of Classification Search
CPC ........ H04N 25/10; H04N 23/95; H04N 25/79; H04N 25/773; G16H 30/00
See application file for complete search history.

(56) References Cited

U.S. PATENT DOCUMENTS

| | | | |
|---|---|---|---|
| 2015/0163429 A1* | 6/2015 | Dai | H04N 25/772 348/295 |
| 2021/0037203 A1* | 2/2021 | Maekawa | H04N 25/773 |
| 2021/0123802 A1* | 4/2021 | Ryoki | G01J 1/0228 |
| 2021/0389176 A1* | 12/2021 | Yamazaki | H04N 25/773 |
| 2022/0190011 A1* | 6/2022 | Yamazaki | H01L 27/14627 |

* cited by examiner

*Primary Examiner* — Hung H Lam
(74) *Attorney, Agent, or Firm* — Canon U.S.A., Inc. IP Division (57) ABSTRACT

A photoelectric conversion device including a pixel equipped with a photoelectric conversion circuit configured to output a signal in response to incidence of a photon includes a first measurement circuit, a second measurement circuit, a selection circuit, and a selection circuit. The first measurement circuit is configured to measure the signal output from the pixel. The second measurement circuit is configured to measure time from when the first measurement circuit starts measuring the signal until a measured value measured by the first measurement circuit reaches a first threshold value. The selection circuit is configured to switch a first measurement circuit to be connected to the second measurement circuit among a plurality of first measurement circuit. The control circuit is configured to control timing of switching a connection of the second measurement circuit by the selection circuit.

18 Claims, 8 Drawing Sheets

PHOTOELECTRIC CONVERSION DEVICE, IMAGING DEVICE, CONTROL METHOD, AND STORAGE MEDIUM

BACKGROUND

Technical Field

The present exemplary embodiment relates to a photoelectric conversion circuit configured to output a signal corresponding to an incident photon.

Description of the Related Art

In recent years, a photoelectric conversion device has been proposed that digitally counts the number of photons incident on an avalanche photodiode, and outputs the counted value as a photoelectrically converted digital signal from a pixel.

United States Patent Application Publication No. 2015/0163429 discusses a structure provided with a time counter configured to measure time in addition to a photon counter configured to count photons. The time counter measures time from the start of the measurement of the photon counter until the number of photons reaches a predetermined value, and calculates the pixel value from the measured time.

United States Patent Application Publication No. 2015/0163429 discusses that the photon counter and the time counter are provided for each pixel, and thus, the circuit scale is increased.

SUMMARY

The present exemplary embodiment has been made in view of such an issue, and provides a technique of suitably performing pixel reading processing while suppressing an increase in circuit scale.

According to an aspect of the disclosure, a photoelectric conversion device including a pixel equipped with a photoelectric conversion circuit configured to output a signal in response to incidence of a photon includes a first measurement circuit, a second measurement circuit, a selection circuit, and a control circuit. The first measurement circuit is configured to measure the signal output from the pixel. The second measurement circuit is configured to measure time from when the first measurement circuit starts measuring the signal until a measured value measured by the first measurement circuit reaches a first threshold value. The selection circuit is configured to switch the first measurement circuit to be connected to the second measurement circuit among a plurality of first measurement circuit. The control circuit is configured to control timing of switching a connection of the second measurement circuit by the selection circuit.

Further features of the disclosure will become apparent from the following description of exemplary embodiments with reference to the attached drawings.

DESCRIPTION OF THE EMBODIMENTS

Embodiments for carrying out the present exemplary embodiment will be described in detail below. Exemplary embodiments described below are examples for realizing the present exemplary embodiment, and should be appropriately modified or changed depending on the configuration of the device to which the present exemplary embodiment is applied and various conditions. The present exemplary embodiment is not limited to the embodiments below. In all the figures, those having the same function are given the same number, and repeated description is omitted. In the following, the term "unit" may refer to a software context, a hardware context, or a combination of software and hardware contexts. In the software context, the term "unit" refers to a functionality, an application, a software module, a function, a routine, a set of instructions, or a program that can be executed by a programmable processor such as a microprocessor, a central processing unit (CPU), or a specially designed programmable device or controller. A memory contains instructions or program that, when executed by the CPU, cause the CPU to perform operations corresponding to units or functions. In the hardware context, the term "unit" refers to a hardware element, a circuit, an assembly, a physical structure, a system, a module, or a subsystem. It may include mechanical, optical, or electrical components, or any combination of them. It may include active (e.g., transistors) or passive (e.g., capacitor) components. It may include digital and/or analog circuits. It may include semiconductor devices having a substrate and other layers of materials having various concentrations of conductivity. It may include a CPU or a programmable processor that can execute a program stored in a memory to perform specified functions. It may include logic elements (e.g., AND, OR) implemented by transistor circuits or any other switching circuits. In the combination of software and hardware contexts, the term "unit" or "circuit" refers to any combination of the software and hardware contexts as described above

Basic Form

Figure 1:
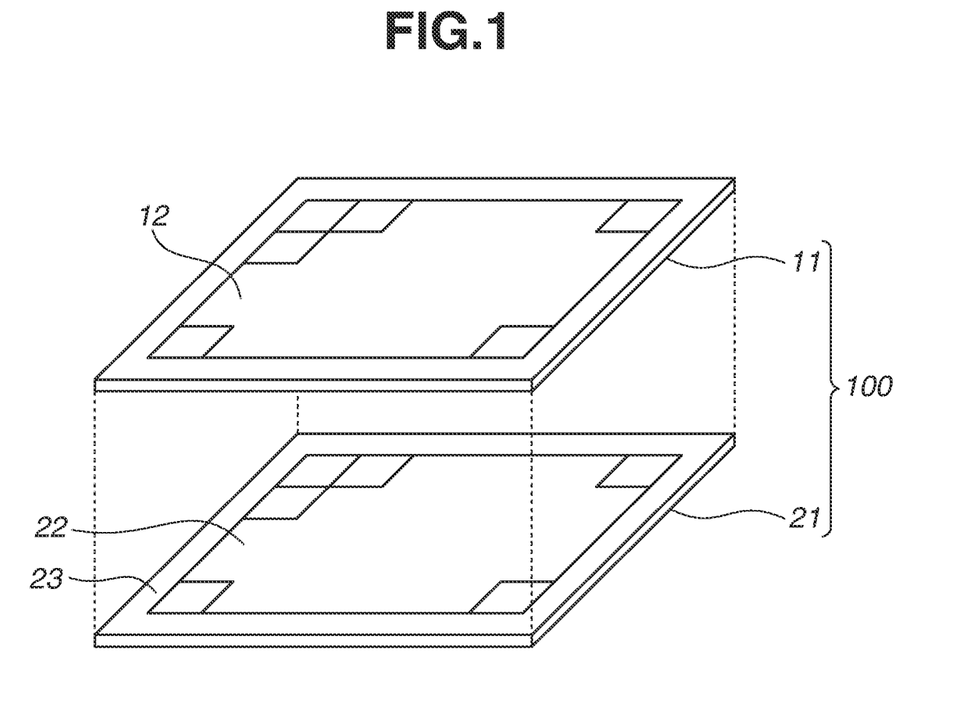
FIG. 1 is a diagram illustrating an example of a hardware configuration of a photoelectric conversion device.

A first exemplary embodiment will be described. FIG. 1 is a diagram illustrating an example of a configuration of a photoelectric conversion device according to the present exemplary embodiment. The photoelectric conversion device 100 is formed by stacking two chips, namely, a sensor chip 11 and a circuit chip 21, and electrically connecting the two chips. The sensor chip 11 includes a pixel area 12. The circuit chip 21 includes a pixel circuit area 22 in which signals detected in each pixel of the pixel area 12 are processed in parallel and a peripheral circuit area 23 in which signals from the pixel circuit area 22 are read and the pixel circuit area 22 is controlled.

Pixel Board

Figure 2:
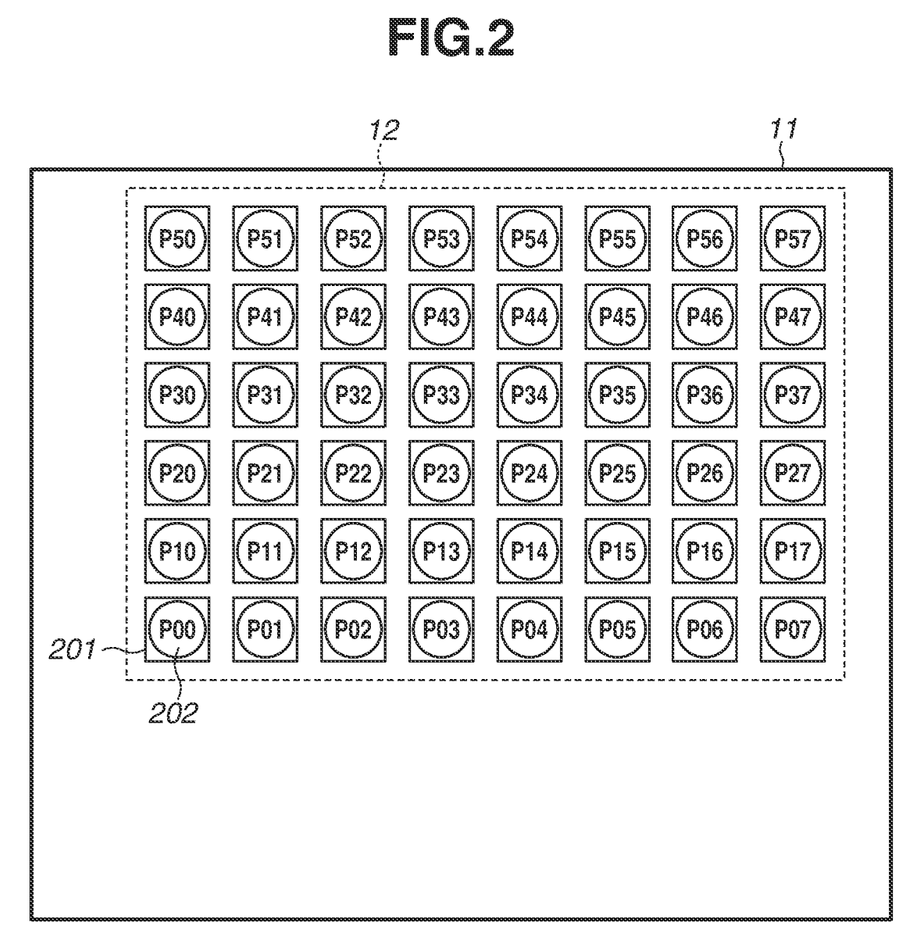
FIG. 2 is a diagram illustrating an example of a sensor chip of the photoelectric conversion device.

FIG. 2 is a diagram illustrating an example of a configuration of the sensor chip 11. The pixel area 12 of the sensor chip 11 includes a plurality of pixels 201 two-dimensionally arranged in a plurality of rows and columns. The pixels 201 have a photoelectric conversion unit or circuit including an avalanche photodiode 202 (hereinafter, referred to as an APD) that outputs a signal according to incident photons. FIG. 2 illustrates 48 pixels 201 arranged in 6 rows from the 0th row to the 5th row, and 8 columns from the 0th column to the 7th column together with a code indicating the row number and the column number. For example, the code "P14" is assigned to a unit pixel arranged in the first row and the fourth column. The number of rows and columns of the pixel array in the pixel area 12 is not particularly limited.

Circuit Board

Figure 3:
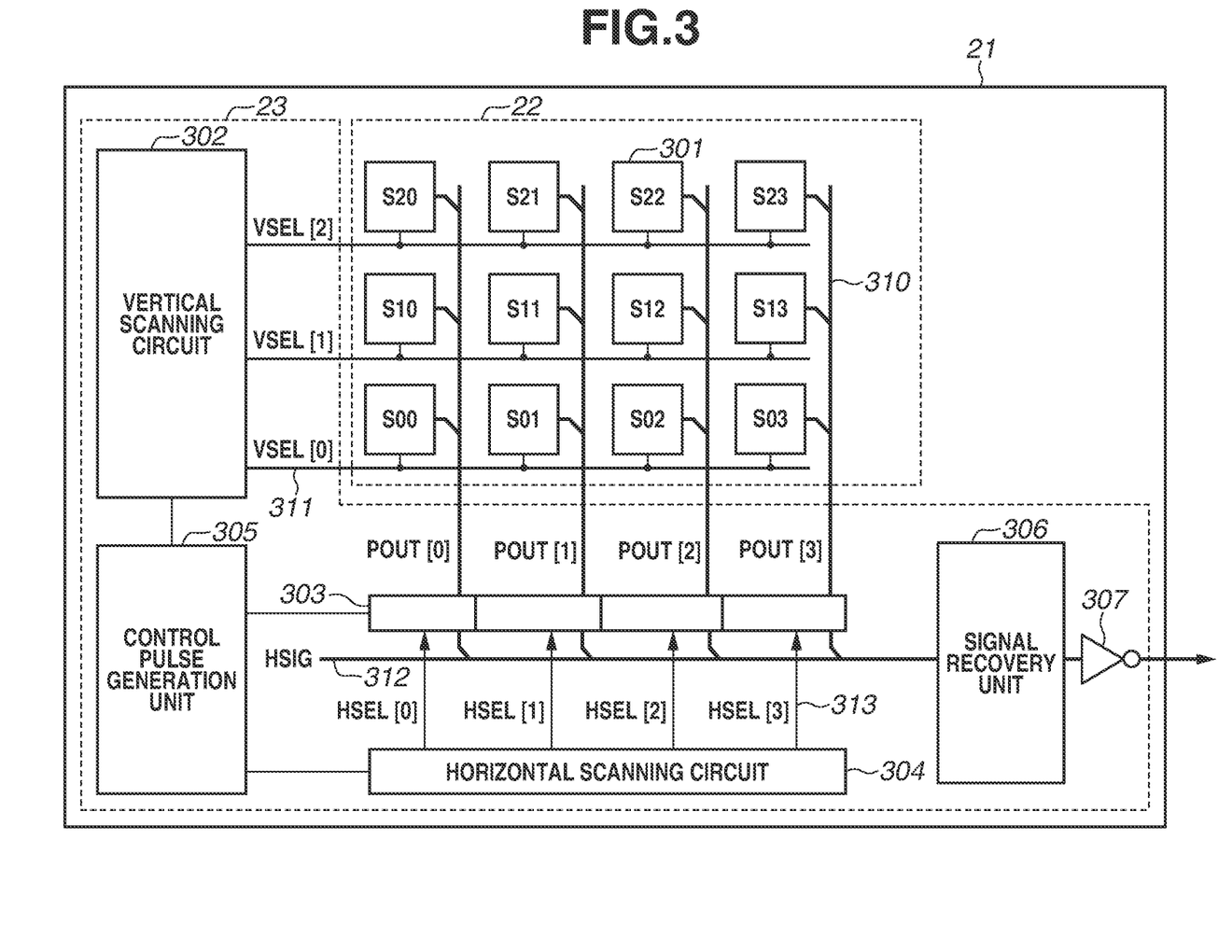
FIG. 3 is a diagram illustrating an example of a circuit chip of the photoelectric conversion device.

FIG. 3 is a diagram illustrating an example of a configuration of the circuit chip 21. The circuit chip 21 includes a pixel circuit area 22 and a peripheral circuit area 23.

Pixel Circuit Area

A plurality of pixel circuit areas 22 is two-dimensionally arranged in a plurality of rows and columns, and includes signal processing units or circuits 301 corresponding to the pixels 201 of the sensor chip. FIG. 3 illustrates 12 signal processing circuits 301 arranged in three rows from the 0th row to the second row, and four columns from the 0th column to the third column together with a code indicating the row number and the column number. For example, the code "S22" is assigned to the signal processing circuit 301 arranged in the second row and the second column. The number of rows and columns of the signal processing circuit array in the pixel circuit area 22 is not particularly limited. The signal processing circuit is provided with a photon counter 403 configured to count the number of photons and a time counter 406 configured to measure time. In the photoelectric conversion device according to the present exemplary embodiment, the photon counters 403a to 403d are provided for each pixel, but the time counter 406 is shared by a plurality of pixels. That is, in the pixel area 12, a set of a plurality of pixels is regarded as one partial pixel area, and while the photon counters 403a, 403b, 403c, and 403d are arranged for each pixel, the time counter 406 is arranged for each partial pixel area. With such a configuration, the circuit scale can be reduced. The details will be described below.

Peripheral Circuit Area

The peripheral circuit area 23 includes a vertical scanning circuit 302, a column circuit 303, a horizontal scanning circuit 304, a control pulse generation unit or circuit 305, a signal restoration unit or circuit 306, and a signal output circuit 307. A vertical selection line 311 VSEL is arranged in each row of the signal processing circuit array of the pixel circuit area 22 extending in a first direction (horizontal direction in FIG. 3). The vertical selection lines 311 VSEL are connected to each of the signal processing circuits 301 arranged in the first direction to form a signal line. The first direction in which the vertical selection lines 311 VSEL extend may be referred to as a row direction or a horizontal direction. FIG. 3 illustrates the control lines VSEL together with a code indicating the row number. For example, the code "VSEL[1]" is assigned to the control line of the first row. The vertical selection line 311 VSEL of each row is connected to the vertical scanning circuit 302. The vertical scanning circuit 302 supplies vertical selection signals that selectively drive the signal processing circuits 301, to the signal processing circuits 301, via the vertical selection lines 311 VSEL. In the present exemplary embodiment, the vertical selection lines 311 are divided into vertical selection lines for reading the signals of the plurality of the signal processing circuits 301 in each row, and vertical selection lines for resetting the signals of the plurality of the signal processing circuits 301 in each row.

A vertical signal line 310 is arranged in each column of the signal processing circuit array of the pixel circuit area 22 extending in a second direction (vertical direction in FIG. 3) intersecting with the first direction. The vertical signal lines 310 are connected to each of the signal processing circuits 301 arranged in the second direction to form a common signal line. The second direction in which the vertical signal lines 310 extend may be referred to as a column direction or a vertical direction. FIG. 3 illustrates the vertical signal lines 310 together with a code indicating the row number. For example, the code "POUT[3]" is assigned to the vertical signal line 310 of the third column. The vertical signal line 310 of each row has n number of signal lines that output digital signals of n bits.

The horizontal scanning circuit 304 supplies, to the column circuit 303, a horizontal selection signal that reads a signal from the column circuit 303. The horizontal scanning circuit 304 supplies a control signal to the column circuit 303 of each column via a horizontal selection line 313 HSEL. Upon receiving the horizontal selection signals from the horizontal scanning circuit 304, the column circuits 303 sequentially output the held signals to the horizontal output circuit 307 via a signal line 312 HSIG and a signal restoration unit or circuit 306. FIG. 3 illustrates the horizontal selection lines HSEL together with a code indicating the column number. For example, the code "HSEL[3]" is assigned to the horizontal selection line of the third column.

The control pulse generation circuit 305 supplies control pulse signals to control an operation and timing of the vertical scanning circuit 302, the horizontal scanning circuit 304, and the column circuit 303. At least some of the control pulse signals to control an operation and timing of the vertical scanning circuit 302, the horizontal scanning circuit 304, and the column circuit 303 may be supplied from the outside of the photoelectric conversion device. The signal restoration circuit 306 calculates the pixel value from the measured value measured by the time counter 406 and outputs the value to the horizontal output circuit 307.

The horizontal output circuit 307 outputs a signal corresponding to the pixel value restored by the signal restoration circuit 306 as an output signal SOUT of the photoelectric conversion device. The value measured by the time counter may be output as it is, that is, the signal restoration circuit 306 may be provided outside the photoelectric conversion device.

<Pixel Circuit>

Figure 4A:
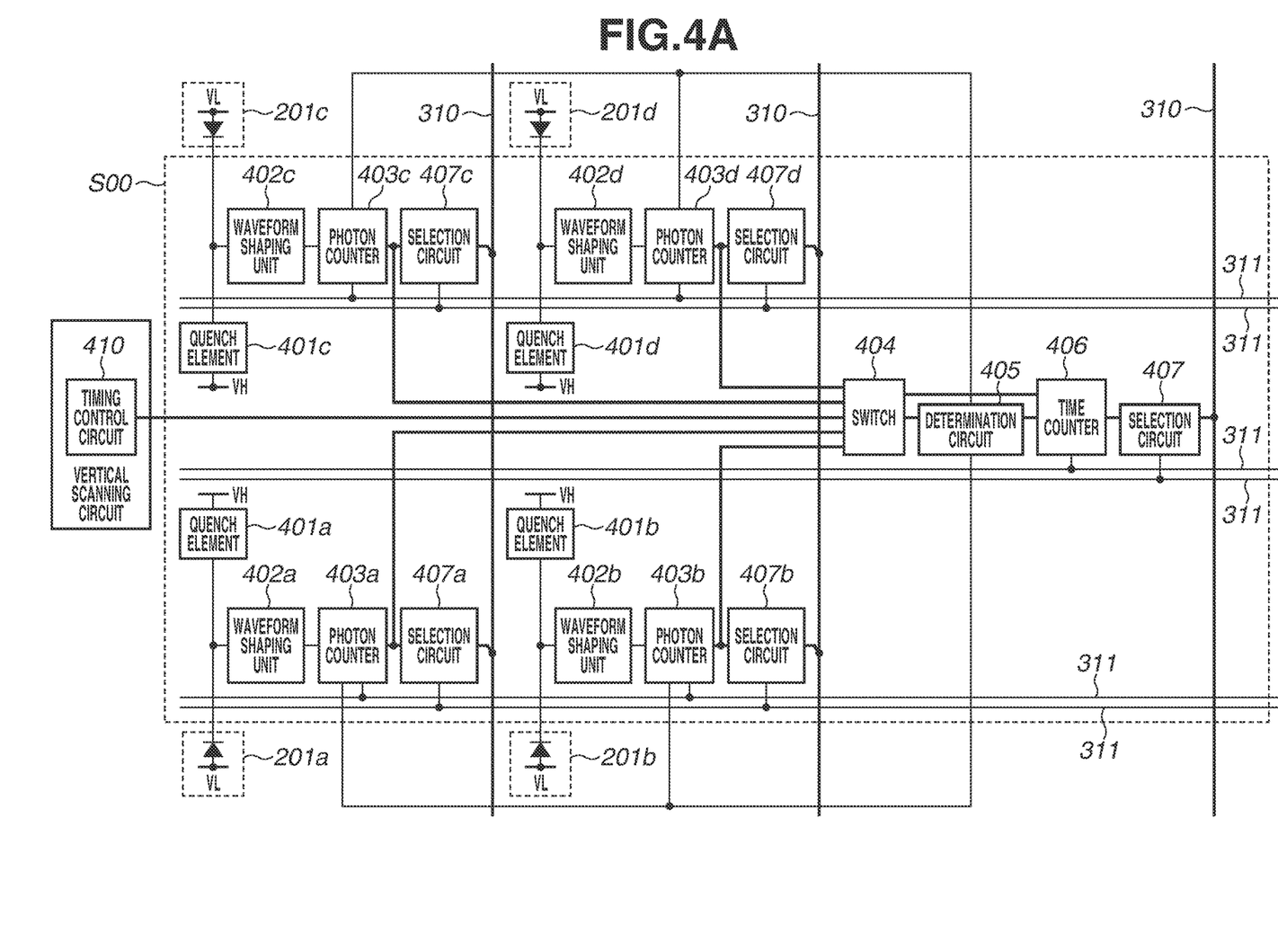
FIG. 4A is a diagram illustrating an example of an equivalent circuit of a pixel and signal processing circuit in the photoelectric conversion device.

FIG. 4A is an example of an equivalent circuit and a block diagram of a pixel 201 of FIG. 2 and a signal processing unit or circuit 301 of FIG. 3. FIG. 4A illustrates one signal processing circuit 301 and four pixels 201a, 201b, 201c, and 201d corresponding to the signal processing circuit 301. A set of a plurality of pixels is regarded as one partial pixel area, and while the photon counters 403a, 403b, 403c, and 403d are arranged for each pixel, the time counter 406 is arranged for each partial pixel area. In the following, when it is necessary to distinguish the four pixels, the codes a, b, c, and d are assigned, and when it is not necessary to distinguish the four pixels, such codes are omitted.

The pixel 201 in the sensor chip 11 includes an APD 202 being a photoelectric conversion unit or circuit. When a photon is incident on the APD 202, a charge pair is generated by photoelectric conversion. A voltage VL (first voltage) is supplied to the anode of the APD 202. A voltage VH (second voltage) higher than the voltage VL supplied to the anode is supplied to the cathode of the APD 202 via the switch element 408. A reverse bias voltage is supplied to the anode and the cathode so that the APD 202 performs an avalanche multiplication operation. By supplying such a voltage, the electric charge generated by the incident light causes an avalanche multiplication, and an avalanche current is generated.

In a case where a reverse bias voltage is supplied, there are the Geiger mode in which the APD 202 is operated at a potential difference between the anode and the cathode being larger than the breakdown voltage, and the linear mode in which the APD 202 is operated at a potential difference between the anode and the cathode being near or less than the breakdown voltage. An APD operated in the Geiger mode is called a Single Photon Avalanche Diode (SPAD). For example, the voltage VL (the first voltage) is −30 V, and the voltage VH (the second voltage) is 1 V.

The signal processing circuit 301 in the circuit chip 21 includes a quench element 401, a waveform shaping unit or circuit 402, a photon counter 403, a switch 404, a determination circuit 405, a time counter 406, a selection circuit 407, and a timing control circuit 410.

The quench element 401 is connected to the APD 202 and a power source configured to supply the voltage VH. The quench element 401 has a function of converting the change in the avalanche current generated in the APD 202 into a voltage signal. The quench element 401 functions as a load circuit (quenching circuit) when the signal is multiplied in avalanche multiplication, suppresses the voltage supplied to the APD 202, and acts to suppress the avalanche multiplication (quenching operation).

The waveform shaping circuit 402 shapes the potential change of the cathode of the APD 202 obtained at the time of photon detection, and outputs a pulse signal. An inverter circuit or a buffer circuit, for example, is used as the waveform shaping circuit 402.

The photon counter 403 is a photon counter configured to measure the number of photons incident on a pixel, and count the pulse signals output from the waveform shaping circuit 402 up to, for example, a first threshold value Cx. The photon counter 403 resets the measured value when a predetermined control signal is supplied via the vertical selection lines 311.

The APD 202, the quench element 401, the waveform shaping circuit 402, and the photon counter 403 described above are provided for each pixel. On the other hand, one OR circuit 404, one determination circuit 405, and one time counter 406, which will be described below, are provided for four pixels (that is, one partial pixel area). One selection circuit 407 is arranged for each photon counter 403, and one is provided for the time counter 406.

The switch 404, the determination circuit 405, and the timing control circuit 410 have a role of connecting the photon counter having the largest measured value among the four photon counters 403a, 403b, 403c, and 403d to the time counter 406. For example, at the start of counting, the photon counter 403a and the time counter 406 are connected by the switch 404. During the counting of photons, the switch 404 may be switched to connect the photon counter 403 having the largest count among the photon counters 403a, 403b, 403c, and 403d, to the time counter 406. The details will be described below.

The determination circuit 405 determines whether the measured value of the photon counter 403 connected to the time counter 406 has reached the first threshold value Cx. The time counter 406 measures time from when the photon counter 403 starts measuring the signals output from the pixels until the measured value (measured value) reaches the first threshold value Cx, and outputs the measured time as a pixel value. That is, when the determination circuit 405 determines that the measured value of the photon counter 403 has reached the first threshold value Cx, the determination circuit 405 outputs "1", and in response, the time counter 406 holds the measured value of time at that point as the pixel value. At a timing when the request signal sent from the request circuit (not illustrated) arrives, the held measured value of the time counter 406 is sent to the peripheral circuit.

The output of the determination circuit 405 is also connected to the four photon counters 403a, 403b, 403c, and 403d, and when the determination circuit 405 outputs "1", photon counting is stopped in all the four photon counters, and the photon measurement value of each photon counter is held.

The timing control circuit 410 controls timing of switching the connection of the time counter 406 based on a predetermined condition. For example, the connection may be switched at regular intervals, or the timing may be determined based on the measured value of the photon counters. The detailed operation will be described below. Photons can be efficiently measured by switching the connection of the time counter shared by multiple photon counters based on the timing. FIG. 4A illustrates an example in which the timing control circuit is arranged for each partial pixel area, however, the timing control circuit may be arranged for each pixel.

<Description of Effect>

As described above, the time counter 406 is connected to the photon counter 403 having the largest count among the photon counters 403a, 403b, 403c, and 403d.

For this reason, the time counter 406 measures the time from the time when light incidence is started on the pixel having the largest amount of light incident per unit time among the pixels 201a, 201b, 201c, 201d to the time when the pixel is saturated.

The shorter the time until saturation, the larger the amount of light incident on the pixel per unit time (brighter). Accordingly, by measuring the time until saturation, it is possible to acquire the brightness information about the brightest pixel among the four pixels from the measured value of the time counter 406.

Among the four photon counters, the measured value of the brightest pixel is always the first threshold value, but for the other three photon counters, the measured value is the photon measurement value of each photon counter when the measured value of the brightest pixel reaches the first threshold value. For this reason, it is possible to acquire, from the measured values measured by the photon counter 403, the brightness information relative to the brightest pixel of three pixels other than the brightest pixel among the four pixels. Accordingly, by combining the measured value of the time counter 406 and the measured value of the photon counter, it is possible to acquire the brightness information about all four pixels. The restoration process of a specific pixel signal will be described below.

Selection Circuit

The selection circuit 407 switches the electrical connection and disconnection between the photon counter 403, the time counter 406 and the vertical signal line 310 by the vertical selection signal VSEL that is supplied from the vertical scanning circuit 302 in FIG. 3 via the vertical selection line 311 and that reads the nth row. The sequentially read pixel measurement values and time measurement values are sent to the column circuit 303, and are output to the outside of the photoelectric conversion device 100 via the signal restoration circuit 306 and the horizontal output circuit 307. After the pixel measurement values and the time measurement values are read by the selection circuit 407 using the selection signal for reading supplied from the vertical selection lines 311, the photon counter and the time counter are reset by the reset signal supplied via the vertical selection lines 311, and each counter resumes counting.

In FIG. 4A, in addition to the vertical signal line 310 for the photon counter of each column, the vertical signal line 310 for the time counter is separately provided, but another configuration may be used.

For example, the photon measurement value of the brightest pixel among the four pixels must always matches the first threshold value, and therefore, instead of the photon measurement value of the brightest pixel, the time measurement value may be read.

Specifically, the time measurement value may be read when the control signal for reading the photon measurement value of the pixel to which the time counter is connected arrives via the vertical selection signal VSEL. Such a configuration is preferable because the amount of signals to be read can be reduced and the power consumption can be reduced.

A flag signal that identifies the pixel having the measured value that has reached the first threshold value among the four pixels, the time measurement value of the pixel that has reached the first threshold value, and the photon measurement values of the three pixels that have not reached the first threshold value may be collectively output to one signal line using a multiplexer circuit or the like.

Switching the Photon Counter

A first modification will be described. Methods of switching the photon counter to which the time counter is connected by the switch 404 during the counting of photons will be described. Firstly, as the first method, a method of sequentially switching the switch of each pixel by using a peripheral scanning circuit will be described. In a case where such a method is used, the timing control circuit 410 configured to control timing of selecting the pixel on which time measurement is to be performed is located in the peripheral scanning circuit as illustrated in FIG. 4A.

As described above, the time counter 406 counts time until the measured value of any of the photon counters 403a, 403b, 403c, and 403d reaches the first threshold value Cx. Accordingly, the switch 404 must compare the measured values of the photon counters 403a, 403b, 403c, and 403d before the measured values of the photon counters reach a specific threshold value and a threshold value of the time counter (first predetermined time).

The photoelectric conversion device 100 sends request signals to the signal processing circuit 301 of each pixel at regular intervals (second predetermined time shorter than the first predetermined time) from a request signal transmission circuit in the vertical scanning circuit 110 in FIG. 3 via the vertical selection lines 311. When the signal processing circuit 301 receives the request signal from the request signal transmission circuit, the determination circuit 405 determines whether one of the measured values of the four photon counters 403a, 403b, 403c, and 403d has reached a second threshold value smaller than a first threshold value, and sends results of the determination to the vertical scanning circuit 110. Upon receiving the results of the determination, the vertical scanning circuit 110 switches the connection destination of the time counter to the photon counter having the measured value that has reached the second threshold value.

By sending the request signal multiple times until one frame is completed, the connection destination of the time counter can be switched at the time the largest measured value among the four photon counters 403a, 403b, 403c, and 403d reaches the second threshold value. That is, the connection destination of the time counter can be switched to the brightest pixel before the measured value of the brightest pixel among the four pixels reaches the first threshold value. With such a configuration, it is possible to acquire the brightness information of the brightest pixel among the four pixels from the measured value of the time counter 406.

In other words, the photoelectric conversion device in the present exemplary embodiment suppresses the circuit scale by sharing the time counter in a plurality of pixels. The issues caused by sharing the time counter among a plurality of pixels are solved by switching the connection destination of the time counter during the operation. The issues will be described below.

Figure 5A:
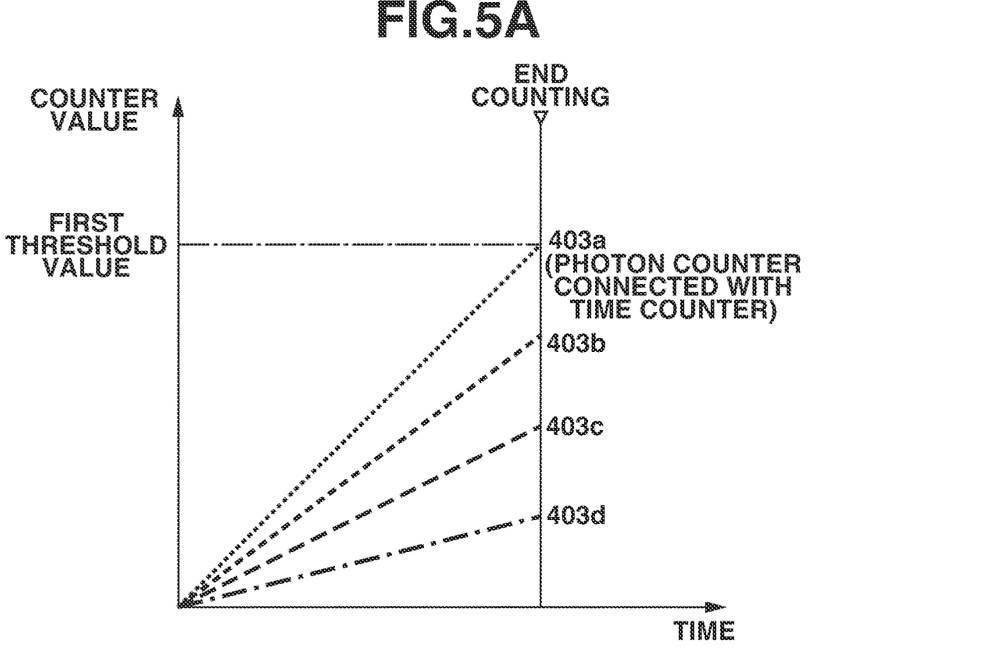
FIG. 5A illustrates a case where the sensitivity of the pixel to which the time counter is connected is the highest among the plurality of pixels sharing the time counter.
Figure 5B:
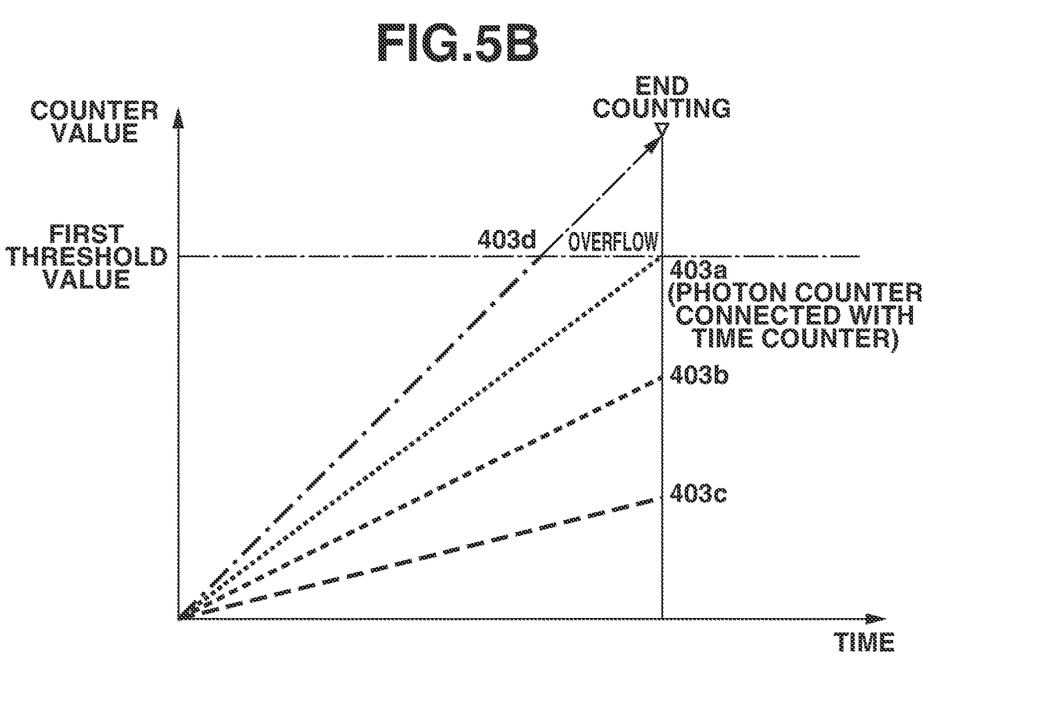
FIG. 5B illustrates a case where there is another pixel having a sensitivity higher than the sensitivity of the pixel to which the time counter is connected among the plurality of pixels sharing the time counter.

FIG. 5A illustrates a case where the sensitivity of the pixel to which the time counter is connected is the highest among the plurality of pixels sharing the time counter. On the other hand, FIG. 5B illustrates a case where there is another pixel having a sensitivity higher than the sensitivity of the pixel to which the time counter is connected among the plurality of pixels sharing the time counter.

As illustrated in FIG. 5A, in a case where the pixel sensitivity of the photon counter to which the time counter is connected is the highest, the brightness information about a plurality of pixels can be acquired by measuring time until the photon counter to which the time counter is connected is saturated. On the other hand, as illustrated in FIG. 5B, in a case where there is another pixel having a pixel sensitivity higher than that of the photon counter to which the time counter is connected, the photon counter to which the time counter is not connected becomes saturated before the photon counter to which the time counter is connected is saturated. In such a case, even by measuring the time until the photon counter to which the time counter is connected is saturated, it is not possible to acquire the brightness information about the pixels that have already been saturated. As described above, in a case where the time counter is shared by a plurality of pixels, the brightness information may not be acquired correctly depending on the subject.

To solve this issue, the photoelectric conversion device in the present exemplary embodiment switches the connection destination of the time counter to the pixel having the highest pixel sensitivity, so that the photon counter to which the time counter is not connected is not saturated.

Switching the Counter

Figure 4B:
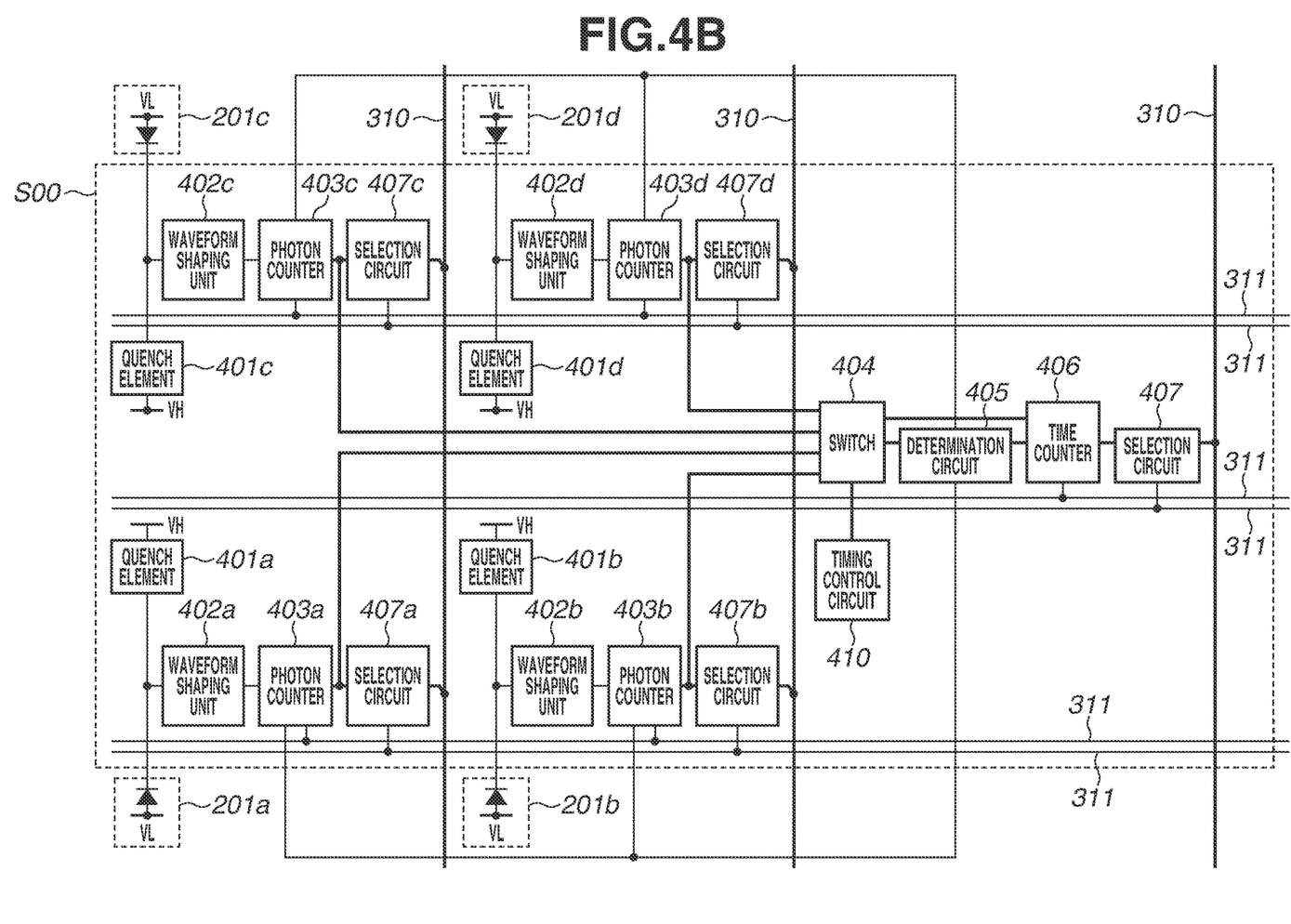
FIG. 4B is a diagram illustrating an example of an equivalent circuit of a pixel and signal processing circuit in the photoelectric conversion device.

A second modification will be described. As the second method, a case where a circuit configured to switch the switch is arranged in each pixel will be described. In a case where such a method is used, the timing control circuit 410 configured to control the timing of selecting the pixel on which time measurement is to be performed is located in the signal processing circuit of each pixel as illustrated in FIG. 4B.

As described above, the time counter 406 counts time until the measured value of the photon counter having the largest count among the photon counters 403a, 403b, 403c, and 403d reaches the first threshold value. For this reason, the switch 404 must compare the measured values of the photon counters 403a, 403b, 403c, and 403d before the measured values of the photon counters reach a specific threshold value.

In the determination circuit 405, it is determined whether any of the measured values of the photon counters 403a, 403b, 403c, and 403d has reached a second threshold value smaller than the first threshold value. The connection destination of the time counter switches to the photon counter having the measured value that has reached the second threshold value. For example, if the first threshold value is equal to the saturation level, and the second threshold value is half the saturation level, an OR circuit of the upper two bits of the measured values of the four photon counters is provided in the determination circuit 405, and when the output of the OR circuit is 1, the connection destination of the time counter may be switched.

With such a configuration, it is possible to acquire the brightness information about the brightest pixel among the four pixels from the measured value of the time counter 406.

Performing Switching Operation Multiple Times

A third modification will be described. The switching of the counter may be controlled a plurality of times in one frame. For example, in a case where the difference between the measured values of a plurality of photon counters is small, it may not be possible to predict which photon counter will be saturated first under the influence of photon shot noise. Accordingly, at the time any one of the measured values measured by the plurality of photon counters reaches the second threshold value, in a case where the difference between the measured values of the photon counter A having the largest measured value and the photon counter B having the next largest measured value is smaller than a third threshold value, it may be better to switch the counter again. The third threshold value may be determined by the photon shot noise, and may be, for example, the square root of the second threshold value or about twice the square root of the second threshold value.

Specifically, after switching the counters once, it is determined whether any of the measured values measured by the plurality of photon counters reaches a fourth threshold value larger than the second threshold value and smaller than the first threshold value. The connection destination of the time counter is switched to the photon counter having the measured value that has reached the fourth threshold value. By switching the connection destination of the time counter a plurality of times in this way, the probability of the connection destination of the time counter being the pixel having the highest pixel sensitivity is improved. At this time, the photon counter A and the photon counter B may be the only photon counters configured to determine whether any of the measured values measured by the plurality of photon counters has reached the fourth threshold value. This is because the photon counters other than the photon counters A and B are less likely to be saturated before the photon counters A and B, even if the influence of photon shot noise is taken into consideration.

Signal Restoration Circuit

The signal restoration circuit 306 restores the time measurement values counted by the time counter 406 and the photon measurement values counted by the photon counter 403 to a pixel signal that represents the brightness information about the subject. When the time measurement value is T0 and the photon measurement values of the four pixels 201a, 201b, 201c, and 201d are P1, P2, P3, and P4, the respective pixel signal values C1, C2, C3, and C4 can be determined by the formula below.

$$C1 = K \times P1/T0, C2 = K \times P2/T0$$

$$C3 = K \times P3/T0, C4 = K \times P4/T0$$

K is a natural number, and it is preferable to determine the value so that C1, C2, C3, and C4 do not become less than 1 LSB. Specifically, K may be set as the maximum value of the time measurement value.

Output of Photon Measurement Value after a Fixed Period of Time

A fourth modification will be described. If the measured value of the photon counter to which the time counter is connected does not reach the first threshold value even after a predetermined time (first predetermined time) has elapsed, the determination circuit 405 may stop the time counter 406 and output the photon measurement value at that time. With such a configuration, it is possible to solve the issue of slowing of the frame rate when the brightness of the subject is very dark. The predetermined time is preferably set to the maximum value of the time count.

Spectral Sensitivity, Bayer Arrangement

FIGS. 3 and 4 illustrate examples in which one signal processing circuit 301 is connected to the four pixels 201. In a case where the number of pixels connected to one signal processing circuit 301 is two or more, the circuit scale can be reduced. Specifically, the photon counter may be provided for each pixel, and the time counter may be shared by a plurality of pixels.

Each pixel 201 may have an on-chip color filter and may be configured to acquire spectral information. For example, in a case where a Bayer array color filter is assumed, it is preferable to provide one signal processing circuit 301 for 4 (2×2) pixels because it is possible to acquire the brightness information in circuits of Bayer pixels. That is, it is preferable that the spectral sensitivities are different in at least some of the pixels sharing the time counter.

In a case where the spectral sensitivities of the respective pixels are not different, the pixel count values of the plurality of pixels may reach the first threshold value Cx at the same time. In such a case, the time measurement value at the time when the pixel count values of the plurality of pixels reach the first threshold value Cx is held as the pixel value. At a timing when the request signal sent from the request circuit (not illustrated) arrives, the held measured value of the time counter 406 is sent to the peripheral circuit. Thereafter, the connection destination of the time counter is connected to any of the pixels having the pixel count values that have not reached the first threshold value Cx. The same operation may be repeated every time the pixel count value of the pixel to which the time counter is connected reaches the first threshold value Cx.

In the case of the Bayer array, because the sensitivity of the green pixel is the highest in a general subject, it is preferable to set the initial connection destination of the time counter to the green pixel. Further, in a case where a video of multiple frames is acquired, it is more preferable to compare the values of the red pixel, the green pixel, and the blue pixel of the previous frame, and then in the next frame, connect the initial connection destination of the time counter to the pixel with the highest sensitivity in the previous frame.

Imaging Device

Figure 6:
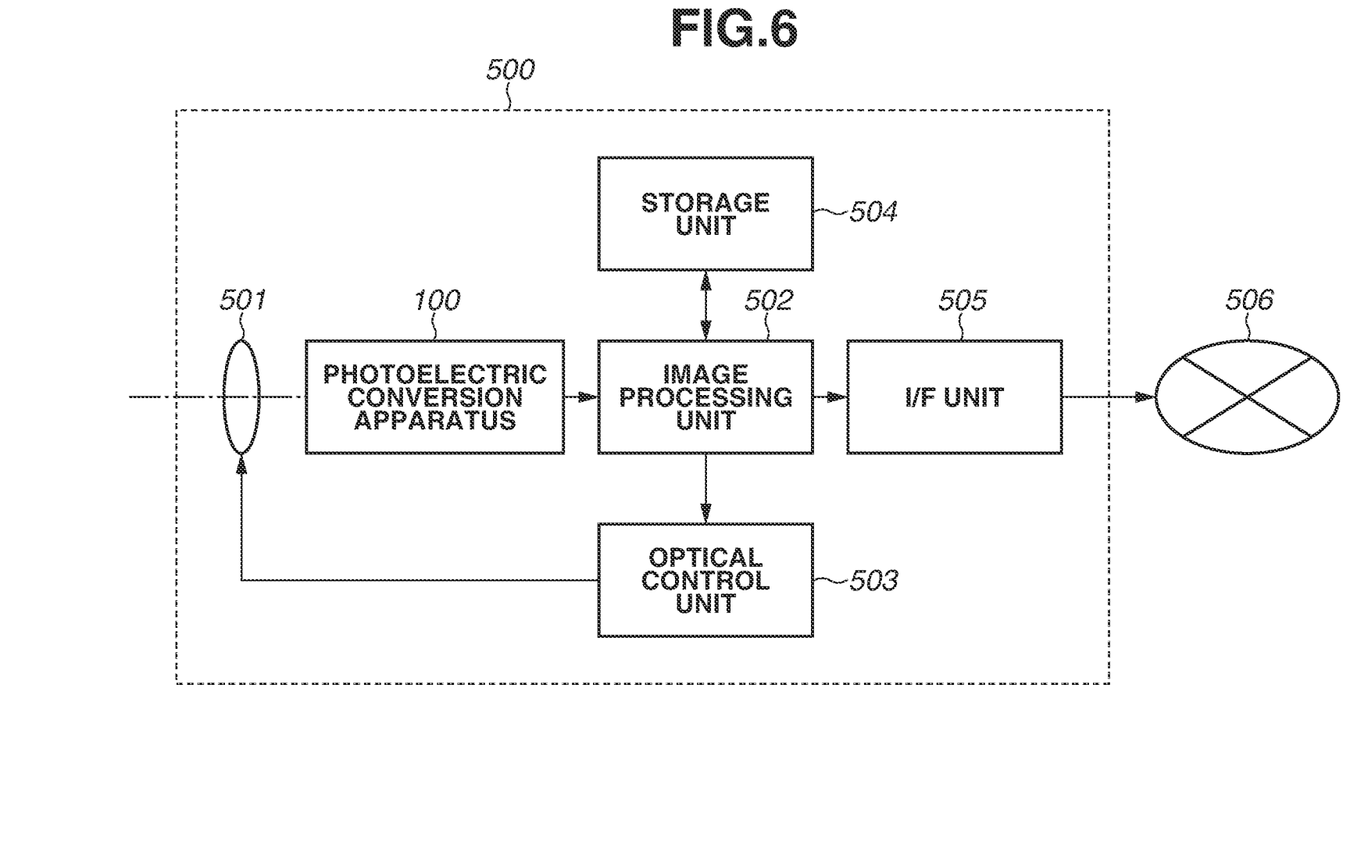
FIG. 6 is a block diagram illustrating an example of a functional configuration of an imaging device including a photoelectric conversion device.

FIG. 6 is a block diagram of an imaging device 500 using the photoelectric conversion device 100.

The imaging device 500 is, for example, a digital camera, which is an imaging device including a photoelectric conversion device 100, and includes a lens 501, an image processing unit or circuit 502, an optical control unit or circuit 503, a storage unit or circuit 504, and a wireless I/F (Interface) unit or circuit 505 as a communication unit or circuit.

The lens 501 forms an optical image of a subject, makes the formed optical image incident on the imaging surface of the photoelectric conversion device 100, and is provided with a focus lens, a zoom lens, a diaphragm, and the like. The photoelectric conversion device 100 captures an optical image formed by the lens 501. The signals read from the photoelectric conversion device 100 are output to the image processing circuit 502. The image processing circuit 502 performs processing such as signal rearrangement, defect pixel correction, noise reduction, color conversion, white balance correction, gamma correction, and data compression on the signals output from the photoelectric conversion device 100 to generate images. The image processing circuit 502 has a built-in CPU as a computer, and functions as a control circuit configured to control the operation of each circuit of the entire imaging device 500 based on a computer program stored in the memory as a storage medium. The optical control circuit 503 controls the focus lens, zoom lens, aperture, and the like provided in the lens 501. A recording medium (not illustrated) is attached to the recording circuit 504, and the images output from the image processing circuit are stored in the storage medium. A memory card or the like is used as the recording medium, for example. A hard disk or the like may be used as the recording medium. The wireless I/F (Interface) circuit 505 as a communication circuit outputs the image signals generated by the image processing circuit 502 to the outside of the imaging apparatus 500. A network 506 is formed of, for example, a plurality of routers, switches, cables, and the like that satisfy communication standards such as Ethernet (registered trademark), and a client controls the imaging device 500 via the network 506.

Flowchart

Figure 7:
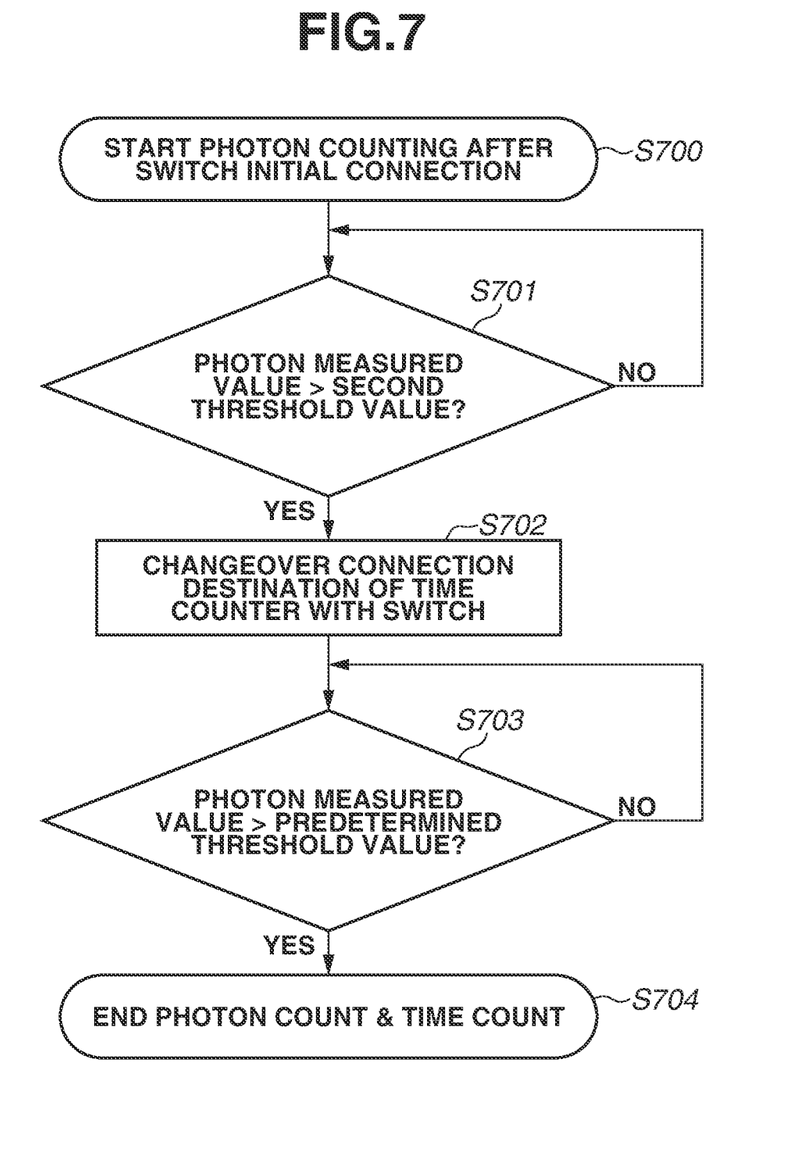
FIG. 7 is a flowchart describing an example of an operation of the photoelectric conversion device.

FIG. 7 is a flowchart describing an operation executed by the photoelectric conversion device according to the present exemplary embodiment. In step S700, the switch 404 performs an initial connection of the time counter 406 with any of the four photon counters 403a, 403b, 403c, and 403d. The initial connection destination may be arbitrarily selected, or the information of the previous frame may be used.

In step S701, the determination circuit 405 determines whether any of the measured values of the four photon counters has reached the second threshold value. If the measured values have not reached the second threshold value (NO in step S701), the counting of photons and time is continued while the connection destination of the time counter remains set as the initial connection. If a measured value has reached the second threshold value (YES in step S701), the processing proceeds to step S702, and the switch 404 switches the connection destination of the time counter to the photon counter having the measured value that has reached the second threshold value.

In step S703, the determination circuit 405 determines whether the measured value of the photon counter to which the time counter after switching is connected has reached the first threshold value. In step S704, the determination circuit 405 stops the counting of time by the time counter when the measured value of the photon counter reaches the first threshold value, and outputs the photon count and time count.

Other exemplary embodiments will be described. In the exemplary embodiment, an example applied to, for example, a digital camera as an imaging device has been described. However, the imaging device includes electronic devices or the like having an imaging function such as a digital movie camera, a smartphone with a camera, a tablet computer with a camera, an in-vehicle camera, a drone camera, a camera mounted on a robot, or a network camera.

The present exemplary embodiment has been described in detail based on its preferred exemplary embodiments, however, the present exemplary embodiment is not limited to the above exemplary embodiments, and various modifications can be made based on the gist of the present exemplary embodiment, which cannot be excluded from the scope of the present exemplary embodiment.

A part or all of the control in the present exemplary embodiment may be supplied to a photoelectric conversion device, an imaging device, or the like via a network or various storage media by a computer program that realizes the functions of the above-described exemplary embodiments. A computer (or a CPU, an MPU, and the like) in the photoelectric conversion device, the imaging device, or the like may read and execute the program. In such a case, the program and the storage medium in which the program is stored constitutes the present exemplary embodiment.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)?), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2021-155380, filed Sep. 24, 2021, which is hereby incorporated by reference herein in its entirety.

What is claimed is:

1. A photoelectric conversion device including a pixel equipped with a photoelectric conversion circuit configured to output a signal in response to incidence of a photon, the photoelectric conversion device comprising:
    a first measurement circuit configured to measure the signal output from the pixel;
    a second measurement circuit configured to measure time from when the first measurement circuit starts measuring the signal until a measured value measured by the first measurement circuit reaches a first threshold value;
    a selection circuit configured to switch a first measurement circuit to be connected to the second measurement circuit among a plurality of first measurement circuits; and
    a control circuit configured to control timing of switching a connection of the second measurement circuit by the selection circuit,
    wherein the first measurement circuit is arranged in each of a plurality of the pixels, and
    wherein the second measurement circuit is arranged in each partial pixel area including a plurality of pixels having different spectral sensitivities from each other.

2. The photoelectric conversion device according to claim 1, wherein the control circuit determines whether to switch the connection of the second measurement circuit by the selection circuit based on measured values measured by the plurality of first measurement circuits at predetermined time intervals.

3. The photoelectric conversion device according to claim 1,
    wherein the control circuit is arranged in each partial pixel area including a plurality of pixels, and determines whether the measured value measured by the first measurement circuit corresponding to the pixel included in the partial pixel area is larger than a second threshold value smaller than the first threshold value, and
    wherein the selection circuit switches the connection to the first measurement circuit whose measured value is larger than the second threshold value.

4. The photoelectric conversion device according to claim 3, wherein the selection circuit connects the second measurement circuit to a first measurement circuit having a largest measured value corresponding to the pixel included in the partial pixel area.

5. The photoelectric conversion device according to claim 1,
    wherein the control circuit is arranged in each pixel, and determines whether the measured value measured by the first measurement circuit corresponding to each of the pixels is larger than a second threshold value smaller than the first threshold value, and
    wherein the selection circuit switches the connection to the first measurement circuit whose measured value is larger than the second threshold value.

6. The photoelectric conversion device according to claim 1, further comprising an output circuit configured to output the measured value measured by the first measurement circuit corresponding to the pixel or a measured value measured by the second measurement circuit.

7. The photoelectric conversion device according to claim 6, wherein the output circuit outputs a measured value measured by a first measurement circuit except for a first measurement circuit having a value that has reached the first threshold value, among the measured values measured by the first measurement circuits respectively corresponding to the plurality of pixels, and the measured value of the second measurement circuit.

8. The photoelectric conversion device according to claim 6, wherein the output circuit outputs a single signal into which the measured value measured by the first measurement circuit included in a partial pixel area including the plurality of pixels and the measured value measured by the second measurement circuit are combined.

9. The photoelectric conversion device according to claim 6, wherein the output circuit outputs the measured value measured by the first measurement circuit corresponding to each of the pixels in a case where the measured value measured by the second measurement circuit reaches a first predetermined time.

10. The photoelectric conversion device according to claim 1, further comprising a signal restoration circuit configured to restore a pixel signal based on the measured value measured by the first measurement circuit corresponding to each of the pixels or the measured value of time measured by the second measurement circuit.

11. The photoelectric conversion device according to claim 1, wherein the second measurement circuit is connected to the first measurement circuit corresponding to the pixel having a highest sensitivity in a previous frame among the plurality of pixels.

12. The photoelectric conversion device according to claim 1, further comprising a red pixel, a blue pixel, and a green pixel,
    wherein the second measurement circuit is connected to the first measurement circuit corresponding to the green pixel in an initial state.

13. The photoelectric conversion device according to claim 1,
    wherein the control circuit determines whether the measured value of the first measurement circuit corresponding to each of the plurality of pixels has reached a second threshold value smaller than the first threshold value based on a request signal, and
    wherein the selection circuit switches a connection destination of the second measurement circuit to the first measurement circuit having a measured value that has reached the second threshold value based on a result of determination.

14. The photoelectric conversion device according to claim 1, wherein the control circuit controls a timing of selecting a pixel for time measurement a plurality of times within one frame.

15. The photoelectric conversion device according to claim 1, wherein the photoelectric conversion circuit includes an avalanche photodiode configured to detect an incident photon.

16. An imaging device comprising:
the photoelectric conversion device according to claim 1.

17. A control method of controlling a photoelectric conversion device including a pixel equipped with a photoelectric conversion circuit configured to output a signal in response to incidence of a photon, a first measurement circuit configured to measure the signal output from the pixel, and a second measurement circuit configured to measure time from when the first measurement circuit starts measuring the signal until a measured value measured by the first measurement circuit reaches a first threshold value, the control method comprising:
  switching a first measurement circuit to be connected to the second measurement circuit among a plurality of first measurement circuits; and
  controlling timing of switching a connection of the second measurement circuit,
  wherein the first measurement circuit is arranged in each of a plurality of the pixels, and
  wherein the second measurement circuit is arranged in each partial pixel area including a plurality of pixels having different spectral sensitivities from each other.

18. A non-transitory storage medium for causing a computer provided in a photoelectric conversion device to execute a control method of controlling the photoelectric conversion device including a pixel equipped with a photoelectric conversion circuit configured to output a signal in response to incidence of a photon, a first measurement circuit configured to measure the signal output from the pixel, and a second measurement circuit configured to measure time from when the first measurement circuit starts measuring the signal until a measured value measured by the first measurement circuit reaches a first threshold value, the control method comprising:
  switching a first measurement circuit to be connected to the second measurement circuit among a plurality of first measurement circuits; and
  controlling timing of switching a connection of the second measurement circuit,
  wherein the first measurement circuit is arranged in each of a plurality of the pixels, and
  wherein the second measurement circuit is arranged in each partial pixel area including a plurality of pixels having different spectral sensitivities from each other.

* * * * *